(12) United States Patent
Belaid-Choucair et al.

(10) Patent No.: US 10,647,752 B2
(45) Date of Patent: May 12, 2020

(54) POLYPEPTIDES CAPABLE OF INHIBITING THE BINDING BETWEEN LEPTIN AND NEUROPILIN-1

(71) Applicants: INSERM (Institut National de la Sante et de la Recherche Medicale), Paris (FR); Fondation Imagine, Paris (FR); Assistance Publique-Hopitaux de Paris (APHP), Paris (FR); Universite Paris Descartes, Paris (FR); Centre National de la Recherche Scientifique (CNRS), Paris (FR); Universite de Bourgogne, Dijon (FR); CNAM—Conservatorie National des Arts et Metiers, Paris (FR)

(72) Inventors: Zakia Belaid-Choucair, Paris (FR); Olivier Hermine, Paris (FR); Matthieu Montes, Paris (FR); Carmen Garrido-Fleury, Dijon (FR); Renaud Seigneuric, Dijon (FR); Guillaume Marcion, Dijon (FR)

(73) Assignees: INSERM (Institut National de la Santé et de la Recherche Medicale), Paris (FR); Fondation Imagine, Paris (FR); Assistance Publique-Hopitaux de Paris (APHP), Paris (FR); Université Paris Descartes, Paris (FR); Centre National de la Recherche Scientifique (CNRS), Paris (FR); Université de Bourgogne, Dijon (FR); CNAM—Conservatoire National des Arts at Metier, Paris (FR)

( * ) Notice: Subject to any disclaimer, the term of this patent is extended or adjusted under 35 U.S.C. 154(b) by 0 days.

(21) Appl. No.: 15/761,828

(22) PCT Filed: Sep. 21, 2016

(86) PCT No.: PCT/EP2016/072352
§ 371 (c)(1),
(2) Date: Mar. 21, 2018

(87) PCT Pub. No.: WO2017/050793
PCT Pub. Date: Mar. 30, 2017

(65) Prior Publication Data
US 2018/0230189 A1 Aug. 16, 2018

(30) Foreign Application Priority Data
Sep. 22, 2015 (EP) ..................................... 15306471

(51) Int. Cl.
*C07K 14/475* (2006.01)
*C07K 14/705* (2006.01)
*C07K 14/575* (2006.01)
*C07K 14/72* (2006.01)
*A61P 35/00* (2006.01)
*A61K 38/18* (2006.01)
*A61K 39/395* (2006.01)
*C07K 16/22* (2006.01)
*A61K 39/00* (2006.01)

(52) U.S. Cl.
CPC ........ *C07K 14/475* (2013.01); *A61K 38/1866* (2013.01); *A61K 39/3955* (2013.01); *A61P 35/00* (2018.01); *C07K 14/5759* (2013.01); *C07K 14/705* (2013.01); *C07K 14/72* (2013.01); *C07K 16/22* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 9,091,651 B2 * | 7/2015 | Kearney | ............ | G01N 33/6848 |
| 2005/0038609 A1 * | 2/2005 | Benner | .............. | G01N 33/6803 702/19 |
| 2014/0141067 A1 * | 5/2014 | Bancel | ................. | A61K 48/005 424/450 |
| 2017/0283502 A1 * | 10/2017 | Sapieha | ............. | A61K 31/7105 |

FOREIGN PATENT DOCUMENTS

| WO | 97/16550 A1 | 5/1997 |
|---|---|---|
| WO | 2015/124588 A1 | 8/2015 |

OTHER PUBLICATIONS

Geneseq Database, 2013, "LC-SRM-MS assay related human tumor marker peptide, SEQ: 4062.", XP002763986, retrieved from EBI accession No. GSP:BAQ10157 Database accession No. BAQ10157.* Aug. 29, 2013; "LC-SRM-MS assay related human tumor marker peptide, SEQ: 4062", XP-002763986, retrieved from EBI accession No. GSP:Baq1057.
Hermine; "La neuropiline un nouveau co-recepteur de la leptine"; L'Agence national de la recherche, Jan. 1, 2013, entire article.
Muenzberg et al.; "Structure, production and signaling of leptin"; Metabolism, vol. 64, No. 1, Sep. 28, 2014, entire document.
Beaulieu et al.; "Leptin Reverts Pro-Apoptotic and Antiproliferative Effects of alpha-Linolenic Acids in BCR-ABL Positive Leukemic Cells: Involvement of P13K Pathway"; PLOs One, vol. 6, No. 10, Oct. 3, 2011, the entire document.

* cited by examiner

*Primary Examiner* — Laura B Goddard
(74) *Attorney, Agent, or Firm* — W&C IP

(57) ABSTRACT

The present invention relates to agents capable of inhibiting the binding between Leptin and Neuropilin-1 (NRP1) and uses thereof in the therapeutic field.

Figure 1:
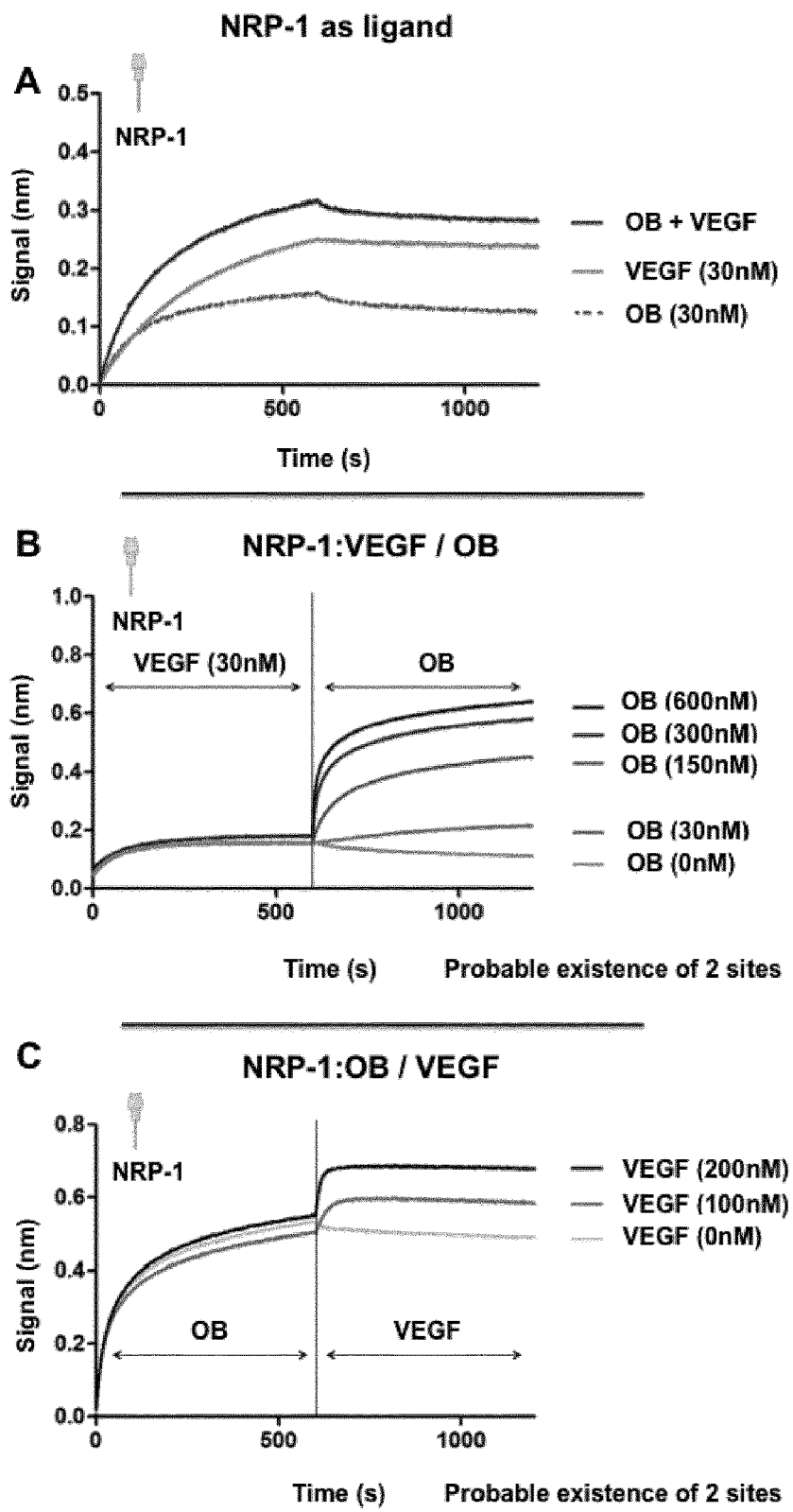

6 Claims, 3 Drawing Sheets
Specification includes a Sequence Listing.

SEQUENCE LISTING

```
<160> NUMBER OF SEQ ID NOS: 4

<210> SEQ ID NO 1
<211> LENGTH: 167
<212> TYPE: PRT
<213> ORGANISM: Homo sapiens

<400> SEQUENCE: 1

Met His Trp Gly Thr Leu Cys Gly Phe Leu Trp Leu Trp Pro Tyr Leu
1               5                   10                  15

Phe Tyr Ala Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 2
<211> LENGTH: 923
<212> TYPE: PRT
<213> ORGANISM: Homo sapiens

<400> SEQUENCE: 2

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
```

```
                370                 375                 380
Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
                660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
            690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
            755                 760                 765

Leu Leu His Lys Ser Leu Lys Leu Tyr Gln Val Ile Phe Glu Gly Glu
            770                 775                 780

Ile Gly Lys Gly Asn Leu Gly Gly Ile Ala Val Asp Asp Ile Ser Ile
785                 790                 795                 800
```

```
Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
                900                 905                 910

Lys Leu Asn Thr Gln Ser Thr Tyr Ser Glu Ala
            915                 920

<210> SEQ ID NO 3
<211> LENGTH: 27
<212> TYPE: PRT
<213> ORGANISM: Homo sapiens

<400> SEQUENCE: 3

Glu Asn Leu Arg Asp Leu Leu His Val Leu Ala Phe Ser Lys Ser Cys
1               5                   10                  15

His Leu Pro Trp Ala Ser Gly Leu Glu Thr Leu
            20                  25

<210> SEQ ID NO 4
<211> LENGTH: 24
<212> TYPE: PRT
<213> ORGANISM: Homo sapiens

<400> SEQUENCE: 4

Glu Gly Asn Lys Pro Val Leu Phe Gln Gly Asn Thr Asn Pro Thr Asp
1               5                   10                  15

Val Val Val Ala Val Phe Pro Lys
            20
```

POLYPEPTIDES CAPABLE OF INHIBITING THE BINDING BETWEEN LEPTIN AND NEUROPILIN-1

FIELD OF THE INVENTION

The present invention relates to agents capable of inhibiting the binding between Leptin and Neuropilin-1 (NRP1) and uses thereof in the therapeutic field.

BACKGROUND OF THE INVENTION

Cytokines, hormones and interactions with their cognate receptors play critical roles in the regulation and homeostasis of various physiological systems. Their dysregulation may lead to diseases related to metabolism, cancer development, and immune or hematopoiesis disorders.

Interactions between hormones, cytokines and their cognate receptors are complex and may require the implication of various co-receptors that modulate in a specific cell type their affinity and the signal transduction. Therefore, depending on the co-receptors involved, hormones/cytokines may compete with each other and may transduce either positive or negative signals for cell growth, survival and specific functions.

Leptin (Lep/OB) is a cytokine-like hormone mainly produced by adipocytes and plays a crucial role in the maintenance of energy balance through its effect in reducing food intake and increasing energy expenditure. It activates receptors (OBR) highly expressed in the brain hypothalamic arcuate nucleus (ARC), a site well known to control body weight (Heike Münzberg and Christopher D Morrison, Metabolism 2014). Hence, defect in leptin receptor signaling leads to severe obesity. Currently, two isoforms of the leptin receptors (OBR) are mainly studied, the short isoform OBRa and the long isoform OBRb.

Leptin mediates most of its effect by activating the long receptor isoform (OBRb), which is the dominant signaling species highly expressed in the brain hypothalamic arcuate nucleus (ARC) (Heike Münzberg and Christopher D Morrison, Metabolism 2014).

However, recent evidences showed that OBR is also expressed in peripheral tissues and that leptin is a more pleiotropic hormone playing a role in other pathophysiological processes including immune regulation, hematopoiesis, cancer development, and metabolism associated disorders including type 2 diabetes, kidney function failure and metabolism associated and age related ocular diseases.

Studies from our group, deciphering the role of adipocytes on the hematopoiesis regulation showed that neuropilin-1 (NRP-1) is overexpressed in femoral fatty bone marrow (Zakia Belaid et al. Heamatologica 2005). NRP-1 is a transmembrane glycoprotein implicated in axonal guidance and angiogenesis through specific ligands and co-receptors SEMA/Plexin and VEGF/VEGFR, respectively (Fujisawa H et al, J Neurobiol 2004 and Soker S et al, Cell 1998). NRP-1 has been shown by our group to be involved in 1) the immune response by participating in the formation of the immune synapse between dendritic cells and T-lymphocytes (R. Tordjman, Yves Lepelletier et al., Nature Immunology 2002), 2) the HTLV1 entry in lymphocytes (David Ghez, Yves Lepelletier et al., Journal of Virology 2005) and 3) the regulation of hematopoiesis by blocking granulopoiesis through the inhibition of the production of granulocyte colony stimulating factor (G-CSF) by macrophages under the influence of adipocytes (Zakia Belaid-Choucair et al. Stem Cell 2008). The latter function was independent of known NRP-1 ligands but involved leptin produced by adipocytes (unpublished data).

NRP-1 needs to form a complex with receptors belonging to the plexin family, which serve as the signal-transducing element for the axonal repulsion and collapse of neuronal growth cones after SEMA binding to the NRP-1/Plexin complex (He and Tessier-Lavigne, Cell 1997). NRP-1 may also interact with VEGF receptors (VEGF-R) forming a complex, which can be activated by VEGF165 for normal developmental angiogenesis (Soker S et al. Cell 1998). Based on both the literature and our results in granulopoiesis regulation, We postulated that the leptin receptor OBR may form a complex with NRP-1. Interestingly, macrophages involved in granulopoiesis inhibition expressed both NRP-1 and OBR at their cell surfaces. NRP-1 and OBR interaction in macrophages was detected by western blotting after NRP-1 co-immunoprecipitation.

By using a well described MDA-MB231 (NRP-1 positive and OBR positive) and T47D (OBR low and NRP-1 negative) breast cancer cell lines transduced either by shNRP-1 or cDNA encoding for NRP-1 we have shown that 1) NRP-1 forms a complex with OBR 2) NRP-1/OBR complex formation is leptin dependent 3) the NRP-1/OBR complex translocates to the nucleus 4) both complex formation and nuclear translocation are dependent on NRP-1 and JAK2 phosphorylation by the Serine/Threonine casein kinase2 (CK2). This finding was confirmed by the inhibition of CK2 by 3 different chemical compounds (TBB, DRB and CX4945) and by RNA silencing that prevented not only NRP-1 and JAK2 phosphorylation but also the formation of the NRP-1/OBR complex.

Leptin has been reported to regulate more than 64 genes including those for growth, cell cycle regulators, extracellular matrix proteins and gene associated with metastasis (Perera C. N et al. J of Endocrinol 2008 and EBM 2008).

Besides a major role in energy homeostasis, the adipokine hormone-like "Leptin" is emerging as a pleiotropic cytokine with pro-angiogenic activity by inducing VEGF and VEGFR2 expression. Multiple signaling molecules modulate the complex interplay between the vascular system and the adipocytes (Yihai Cao, Cell Metabolism 2013).

In breast cancer, leptin is considered as a pro-angiogenic marker (Ruben Rene Gonzalez-Perez et al, Cancers 2013). Anti-VEGF (bevacizumab) treatment of patients with rectal cancer was significantly associated with distant metastasis at three years, which correlated with the up-regulation of NRP-1 and activation of inflammatory pathways (Xu Lei et al, cancer Research 2009).

Interestingly, our functional characterization of NRP-1/OBR complex using breast cancer xenograft model led us to demonstrate that NRP-1 modulates leptin function by decreasing cell proliferation, inducing cell migration and lymph node infiltration. Since leptin has been reported to be pro-angiogenic, we postulated that physiologically, VEGF (a target of Bevacizumab) might play a negative feedback on leptin action during angiogenesis. During treatment with Bevacizumab, VEGF might be unable to reduce leptin action and thus NRP-1 overexpression will be in the favor of NRP-1/OBR and leptin interactions. This complex would lead to a non-canonical signaling involved in metastasis and thus decrease of the overall survival.

As hypothesized, preventing the binding of VEGF to VEGFR by treatment of MDA-MB231 breast cancer cell line with Avastin alone induces in vitro cell migration, as did leptin alone. This effect was further increased when the cells were co-treated with both Avastin and leptin. The increase of leptin effect on cell migration by Avastin treatment raised the question whether VEGF may have a negative feed-back on NRP-1/OBR signaling. Interestingly, we could demonstrate that VEGFs bind to OBR. Thus, we can conclude that blocking VEGF with Avastin increases leptin action and induces metastasis and other known effect of leptin such as inflammation that is also reported during Avastin therapy through an increase of NRP-1OBR complex formation. Interestingly our hypothesis is clearly demonstrated by the increase of NRP-1/OBR complex detection by PLA-HRP technology in MDA-MB231 breast cancer cell line treated with Avastin compared to the control cell. The experiment was done in the presence of normal human serum in order to mimic the physiologic condition during Avastin therapy.

By using a BioLayer Interferometry technology (BLI, http://www.fortebio.com), we were able to demonstrate a direct interaction between recombinant proteins Leptin and NRP-1. In contrast to other NRP-1 ligands such as VEGF, and Sema3A known as competitors, leptin binds directly to NRP-1 but do not compete with VEGF binding. Similarly, VEGF does not prevent leptin binding to NRP-1. These observations suggest that leptin and VEGF have distinct binding domains.

This finding suggests that anti-VEGF therapy should be combined with an anti-leptin therapy in cancer.

This could also implicate disease associated to immune system dysfunction where leptin has been clearly associated in the disease aggravation.

SUMMARY OF THE INVENTION

The present invention relates to agents capable of inhibiting the binding between leptin and NRP-1 and uses thereof in the therapeutic field. In particular, the present invention is defined by the claims.

DETAILED DESCRIPTION OF THE INVENTION

One object of the present invention relates to agent capable of inhibiting the binding between leptin and NRP-1.

As used herein, the term "leptin" has its general meaning in the art and refers to a protein that is secreted by white adipocytes, and which plays a major role in the regulation of body weight. In particular, leptin functions as part of a signaling pathway that can inhibit food intake and/or regulate energy expenditure to maintain constancy of the adipose mass. This protein also has several endocrine functions, and is involved in the regulation of immune and inflammatory responses, hematopoiesis, angiogenesis and wound healing. An exemplary human amino acid sequence of leptin is SEQ ID NO:1.

SEQ ID NO: 1
MHWGTLCGFLWLWPYLFYAQAVPIQKVQDDTKTLIKTIVTRINDISHTQS

VSSKQKVTGLDFIPGLHPILTLSKMDQTLAVYQQILTSMPSRNVIQISND

LENLRDLLHVLAFSKSCHLPWASGLETLDSLGGVLEASGYSTEVVALSRL

QGSLQDMLWQLDLSPGC

As used herein, the term "NRP-1" has its general meaning in the art and refers to the neuropilin-1 receptor. An exemplary human amino acid sequence of NRP-1 is SEQ ID NO:2.

SEQ ID NO: 2
MERGLPLLCAVLALVLAPAGAFRNDKCGDTIKIESPGYLTSPGYPHSYHP

SEKCEWLIQAPDPYQRIMINFNPHFDLEDRDCKYDYVEVFDGENENGHFR

GKFCGKIAPPPVVSSGPFLFIKFVSDYETHGAGFSIRYEIFKRGPECSQN

YTTPSGVIKSPGFPEKYPNSLECTYIVFAPKMSEIILEFESFDLEPDSNP

PGGMFCRYDRLEIWDGFPDVGPHIGRYCGQKTPGRIRSSSGILSMVFYTD

SAIAKEGFSANYSVLQSSVSEDFKCMEALGMESGEIHSDQITASSQYSTN

WSAERSRLNYPENGWTPGEDSYREWIQVDLGLLRFVTAVGTQGAISKETK

KKYYVKTYKIDVSSNGEDWITIKEGNKPVLFQGNTNPTDVVVAVFPKPLI

TRFVRIKPATWETGISMRFEVYGCKITDYPCSGMLGMVSGLISDSQITSS

NQGDRNWMPENIRLVTSRSGWALPPAPHSYINEWLQIDLGEEKIVRGIII

QGGKHRENKVFMRKFKIGYSNNGSDWKMIMDDSKRKAKSFEGNNNYDTPE

LRTFPALSTRFIRIYPERATHGGLGLRMELLGCEVEAPTAGPTTPNGNLV

DECDDDQANCHSGTGDDFQLTGGTTVLATEKPTVIDSTIQSEFPTYGFNC

EFGWGSHKTFCHWEHDNHVQLKWSVLTSKTGPIQDHTGDGNFIYSQADEN

QKGKVARLVSPVVYSQNSAHCMTFWYHMSGSHVGTLRVKLRYQKPEEYDQ

LVWMAIGHQGDHWKEGRVLLHKSLKLYQVIFEGEIGKGNLGGIAVDDISI

NNHISQEDCAKPADLDKKNPEIKIDETGSTPGYEGEGEGDKNISRKPGNV

LKTLDPILITIIAMSALGVLLGAVCGVVLYCACWHNGMSERNLSALENYN

FELVDGVKLKKDKLNTQSTYSEA

In some embodiments, the agents is an isolated, a synthetic or recombinant polypeptide capable of inhibiting the binding between leptin and NRP-1.

In some embodiments, the polypeptide of the present invention comprises an amino acid sequence having at least 90% of identity with the sequence of SEQ ID NO:3 (ENLRDLLHVLAFSKSCHLPWASGLETL) or SEQ ID NO:4 (EGNKPVLFQGNTNPTDVVVAVFPK).

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math, 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci, 8:155-165, 1992; and Pearson et al., Meth. Mol. Biol., 24:307-31, 1994). Altschul et al., Nat. Genet, 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

In some embodiments, the polypeptide of the present invention comprises an amino acid sequence having at least 90% of identity with the sequence of SEQ ID NO:3 comprises at least 27; 28; 29; 30; 31; 32; 33; 34; 35; 36; 37; 38; 39; 40 or more amino acids. In some embodiments, the polypeptide of the present invention comprises an amino acid sequence having at least 90% of identity with the sequence of SEQ ID NO:4 comprises at least 24; 25; 26; 27; 28; 29; 30; 31; 32; 33; 34; 35; 36; 37; 38; 39; 40 or more amino acids. In some embodiments, the polypeptide of the present invention comprises less than 50 amino acids. In some embodiments, the polypeptide of the present invention comprises less than 30 amino acids.

The functional properties of the polypeptide of the present invention, i.e. inhibition of the binding between Leptin and NRP-1, could typically be assessed in any functional assay as described in EXAMPLE.

In some embodiments, the polypeptide of the present invention is fused to at least one heterologous polypeptide to form a fusion protein.

In some embodiments, the polypeptide of the present invention is fused either directly or via a spacer at its C-terminal end to the N-terminal end of the heterologous polypeptide, or at its N-terminal end to the C-terminal end of the heterologous polypeptide. As used herein, the term "directly" means that the (first or last) amino acid at the terminal end (N or C-terminal end) of the polypeptide of the present invention is fused to the (first or last) amino acid at the terminal end (N or C-terminal end) of the heterologous polypeptide. In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide. As used herein, the term "spacer" refers to a sequence of at least one amino acid that links the polypeptide of the invention to the heterologous polypeptide. Such a spacer may be useful to prevent steric hindrances. Typically a spacer comprises 2, 3; 4; 5; 6; 7; 8; 9; 10; 11; 12; 13; 14; 15; 16; 17; 18; 19; or 20 amino acids.

The polypeptides of the present invention are produced by any technique known per se in the art, such as, without limitation, any chemical, biological, genetic or enzymatic technique, either alone or in combination. For instance, knowing the amino acid sequence of the desired sequence, one skilled in the art can readily produce said polypeptides, by standard techniques for production of amino acid sequences. For instance, they can be synthesized using well-known solid phase method, preferably using a commercially available peptide synthesis apparatus (such as that made by Applied Biosystems, Foster City, Calif.) and following the manufacturer's instructions. Alternatively, the polypeptides of the present invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides or fusion proteins of the invention can be used in an isolated (e.g., purified) form or contained in a vector, such as a membrane or lipid vesicle (e.g. a liposome).

In some embodiments, it is contemplated that polypeptides of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. For example, Pegylation is a well-established and validated approach for the modification of a range of polypeptides (Chapman, 2002). The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein (Cunningham-Rundles et. al., 1992); and (e) improved thermal and mechanical stability of the PEGylated polypeptide. Therefore, advantageously, the polypeptides of the invention may be covalently linked with one or more polyethylene glycol (PEG) group(s). One skilled in the art can select a suitable molecular mass for PEG, based on how the pegylated polypeptide will be used therapeutically by considering different factors including desired dosage, circulation time, resistance to proteolysis, immunogenicity, etc. In some embodiments, additional sites for PEGylation can be introduced by site-directed mutagenesis by introducing one or more lysine residues. For instance, one or more arginine residues may be mutated to a lysine residue. In some embodiments, additional PEGylation sites are chemically introduced by modifying amino acids on polypeptides of the invention. In some embodiments, PEGs are conjugated to the polypeptides or fusion proteins through a linker. Suitable linkers are well known to the skilled person.

A further object of the present invention relates to a nucleic acid encoding for a polypeptide of the present invention.

As used herein, the term "nucleic acid" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fiuorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiment, the nucleic acid is included in a suitable vector, such as a plasmid, cosmid, episome, artificial chromosome, phage or viral vector. So, a further object of the present invention relates to a vector and an expression cassette in which a nucleic acid encoding for the polypeptide of the present invention is associated with suitable elements for controlling transcription (in particular promoter, enhancer and, optionally, terminator) and, optionally translation, and also the recombinant vectors into which a nucleic acid in accordance with the invention is inserted. These recombinant vectors may, for example, be cloning vectors, or expression vectors. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Any expression vector for animal cell can be used. Examples of suitable vectors include pAGE107 (Miyaji et al., 1990), pAGE103 (Mizukami and Itoh, 1987), pHSG274 (Brady et al., 1984), pKCR (O'Hare et al., 1981), pSG1 beta d2-4 (Miyaji et al., 1990) and the like. Other examples of plasmids include replicating plasmids comprising an origin of replication, or integrative plasmids, such as for instance pUC, pcDNA, pBR, and the like. Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478. Examples of promoters and enhancers used in the expression vector for animal cell include early promoter and enhancer of SV40 (Mizukami and Itoh, 1987), LTR promoter and enhancer of Moloney mouse leukemia virus (Kuwana et al., 1987), promoter (Mason et al., 1985) and enhancer (Gillies et al., 1983) of immunoglobulin H chain and the like.

A further aspect of the invention relates to a host cell comprising a nucleic acid encoding for the polypeptide of the present invention. In particular, a subject of the present invention is a prokaryotic or eukaryotic host cell genetically transformed with at least one nucleic acid of the present invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". In some embodiments, for expressing and producing polypeptides or fusion proteins of the invention, prokaryotic cells, in particular *E. coli* cells will be chosen. Actually, according to the invention, it is not mandatory to produce the polypeptide or the fusion protein of the invention in a eukaryotic context that will favor post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the fusion protein of the invention. The construction of expression vectors in accordance with the invention, and the transformation of the host cells can be carried out using conventional molecular biology techniques. The polypeptide or the fusion protein of the invention can for example, be obtained by culturing genetically transformed cells in accordance with the invention and recovering the polypeptide or the fusion protein expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the proteins in accordance with the invention.

The present invention also related to an antibody or an aptamer, which specifically binds to a polypeptide of the present invention.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences, which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH:VL heterodimer which is usually expressed from a gene fusion including VH and VL encoding genes linked by a peptide-encoding linker. "dsFv" is a VH::VL heterodimer stabilized by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (i.e. polypeptides of the present invention). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intra-peritoneal, intramuscular, intravenous, intranasal or other routes. A given animal may be immunized with multiple forms of the antigen by multiple routes.

Briefly, the recombinant polypeptide of the present invention may be provided by expression with recombinant cell lines. Recombinant forms of the polypeptides may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods. Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated as Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity-determining regions (CDR1 through CDR5). The CDRs, and in particular the CDR5 regions, and more particularly the heavy chain CDR5, are largely responsible for antibody specificity.

It is now well-established in the art that the non CDR regions of a mammalian antibody may be replaced with similar regions of conspecific or hetero-specific antibodies while retaining the epitope specificity of the original antibody. This is most clearly manifested in the development and use of "humanized" antibodies in which non-human CDRs are covalently joined to human FR and/or Fc/pFc' regions to produce a functional antibody.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor might be selected. The third proposal was that in the positions immediately adjacent to the 3 CDRs in the humanized immunoglobulin chain, the donor amino acid rather than the acceptor amino acid might be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In some embodiments, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al.,/Mol. Biol. 294:151, 1999. The contents of which are incorporated herein by reference.

Fully human monoclonal antibodies can also be prepared by immunizing transgenic mice for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationnaly constrained antibody variable region displayed by a platform protein, such as E. coli Thioredoxin A that are selected from combinatorial libraries by two hybrid methods (Colas et al., 1996).

A further object of the present invention relates to a method of treating a cancer in a subject in need thereof comprising administering to the subject a therapeutically effective amount of a polypeptide, nucleic acid, antibody or aptamer of the present invention.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "cancer" has its general meaning in the art and includes, but is not limited to, solid tumors and blood-borne tumors The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

By a "therapeutically effective amount" is meant a sufficient amount of polypeptide, nucleic acid, antibody or aptamer of the present invention for reaching a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the polypeptide, nucleic acid, antibody or aptamer of the present invention is used in combination with a chemotherapeutic agent for the treatment of cancer. Chemotherapeutic agents include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-1 1); topoisomerase inhibitor RFS 2000; difluoromethylomithine (DMFO); retinoids such as retinoic acid; capecitabine; and pharmaceutically acceptable salts, acids or derivatives of any of the above.

In some embodiments, the polypeptide, nucleic acid, antibody or aptamer of the present invention is used in combination with antiangiogenic agents. As used herein an "antiangiogensis agents" refers to a molecule that inhibits VEGF or VEGFR-mediated angiogenesis, vasculogenesis, or undesirable vascular permeability. For example, an anti-VEGF therapeutic may be an antibody directed against VEGF or VEGFR. An anti-VEGF antibody will usually not bind to other VEGF homologues such as VEGF-B or VEGF-C, or other growth factors such as P1GF, PDGF or bFGF. A preferred anti-VEGF antibody is a monoclonal antibody that binds to the same epitope as the monoclonal anti-VEGF antibody A4.6.1 produced by hybridoma ATCC® HB 10709 and is a high-affinity anti-VEGF antibody. A "high-affinity anti-VEGF antibody" has at least 10-fold better affinity for VEGF than the monoclonal anti-VEGF antibody A4.6.1. Preferably the anti-VEGF antibody is a recombinant humanized anti-VEGF monoclonal antibody fragment generated according to WO 98/45331, including an antibody comprising the CDRs or the variable regions of Y0317. More preferably, anti-VEGF antibody is the antibody fragment known as ranibizumab (LUCENTIS®). The anti-VEGF antibody ranibizumab is a humanized, affinity-matured anti-human VEGF Fab fragment. Ranibizumab is produced by standard recombinant technology methods in *E. coli* expression vector and bacterial fermentation. Ranibizumab is not glycosylated and has a molecular mass of ~48,000 daltons. See WO98/45331 and U.S. 2003/0190317.

Antiangiogenic agents include but are not limited to bevacizumab (rhuMab VEGF, Avastin®, Genentech, South San Francisco Calif.), ranibizumab (rhuFAb V2, Lucentis®, Genentech), pegaptanib (Macugen®, Eyetech Pharmaceuticals, New York N.Y.), sunitinib maleate (Sutent®, Pfizer, Groton Conn.), ramucirumab (Cyramza®, Eli Lilly and Company, Indianapolis, Ind. 46285, USA US License).

Another object of the present invention relates to a pharmaceutical composition comprising the polypeptide, nucleic acid, antibody or aptamer of the present invention and a pharmaceutically acceptable carrier. Typically, the polypeptide, nucleic acid, antibody or aptamer of the present invention can be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to the subjects. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, sub-dermal, transdermal, intrathecal and intranasal administration forms and rectal administration forms. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the present invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide, nucleic acid, antibody or aptamer of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intra-peritoneal administration. In this connection, sterile aqueous media, which can be employed, will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

Figure 2:
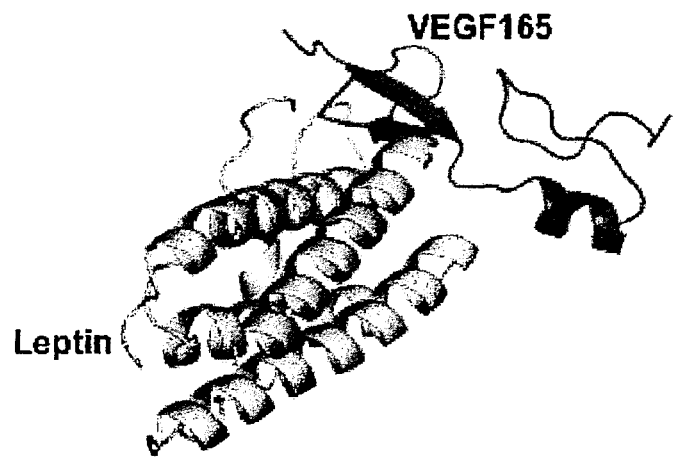
Figure 3:
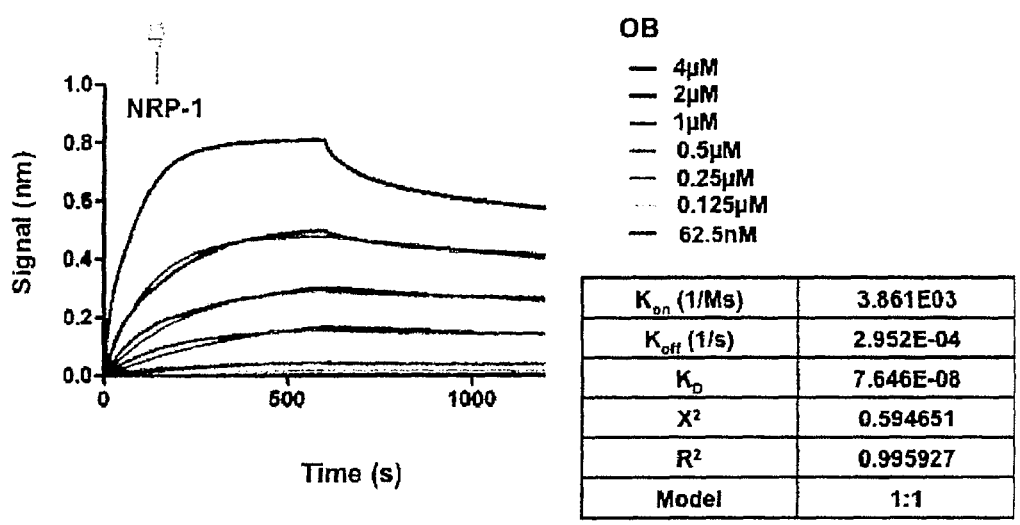
Figure 4:
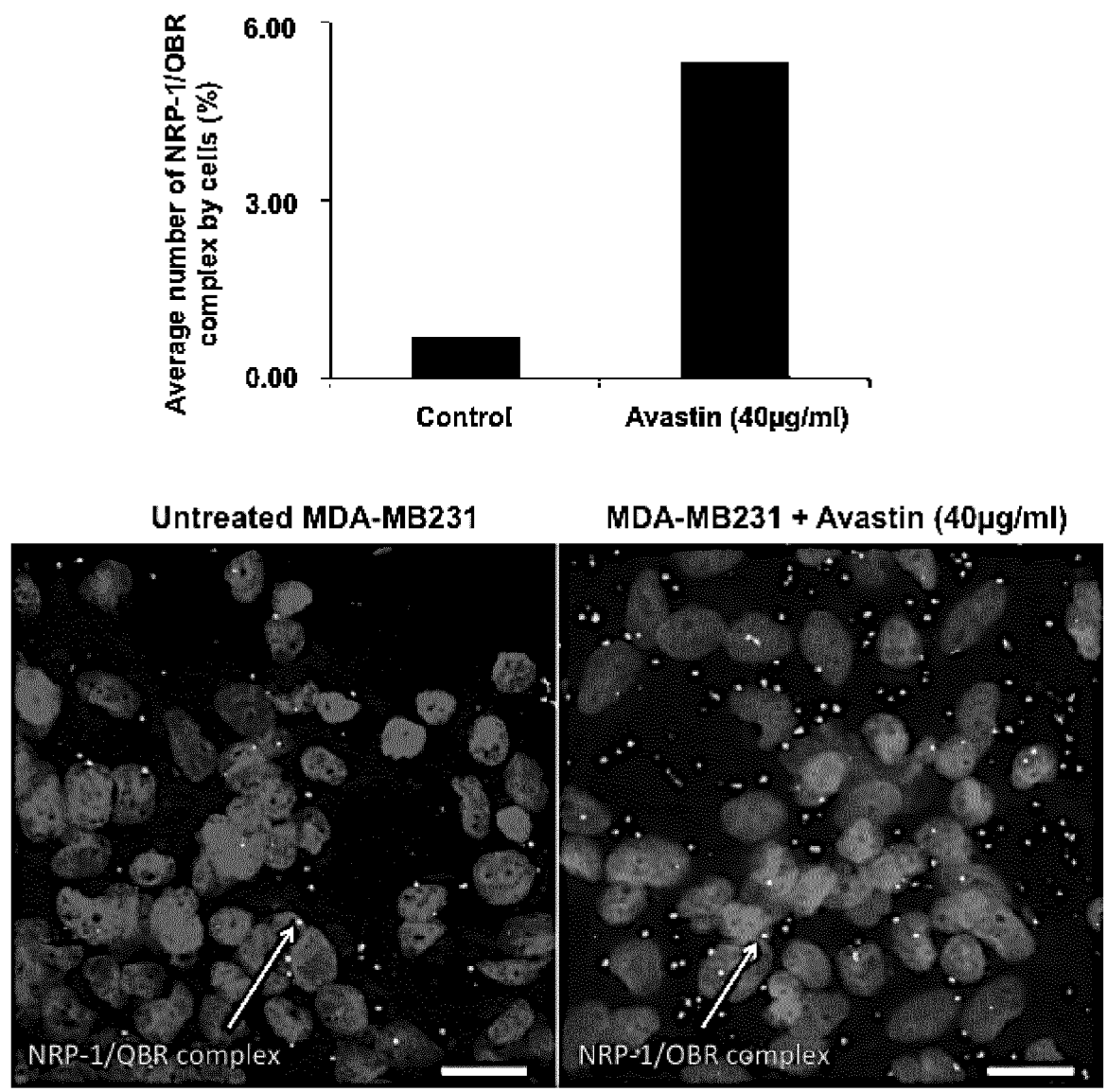

FIG. 1 shows the OB:NRP-1 interaction with VEGF
FIG. 2 shows the OB:VEGF165:NRP1 docking FIG. 3 shows the NRP1:OB peptides interaction FIG. 4 shows the increase of NRP-1/OBR complex formation and MDA—MD231 cell migration following Avastin treatment

EXAMPLE

Material & Methods

Bio-Layer Interferometry

Bio-layer interferometry (BLI) is a label-free technique that is sensitive to an increase of mass bound to the biosensor enabling protein-protein interaction characterization.

Ligands preparation: proteins were incubated in a PBS buffer with a 1:3 ratio molar ratio of biotin (biotin-PEG4-NHS from Pierce EZ kit, prepared following the manufacturer's instructions). Free biotin was removed using a desalting column (Pierce). The biotinylated protein (called ligand) was immobilized onto streptavidin biosensor tips and dipped into wells containing the buffer with the analyte of interest (association) or without (dissociation).

Experimental conditions were as follow: total volume in each well: 200 µl; shake speed: 1,000 rpm. For simple protein:protein interactions an association phase was followed by a dissociation phase. For competition experiments, the association phase was followed by another association phase with a second analyte instead of a dissociation phase.

Sensorgrams were background corrected, smoothed with the Savitzky-Golay algorithm and analyzed using OctetRED instrument software (ForteBio Data Analysis version 7.1). Experimental sensorgrams were first fit to a 1:1 model. The 1:1 model was accepted if the $Chi^2$ test was below 3 and the $R^2$ was above 0.9. When the 1:1 model was rejected, the model with the lowest $Chi^2$ and the highest $R^2$ was then selected.

Molecular Docking Experiment

Preparation of the Protein Structures

The structure of VEGF (PDB ID: 4DEQ) and Leptin (PDB ID: 1AX8) were extracted from the protein databank (ref Berman). Since the leptin structure was mutated in the original PDB (W100E), we reversed the mutation to the wild type leptin with PyMol (ref Delano). Hydrogens and partial charges were added using the dockprep routine from Chimera (ref Pettersen).

Blind Docking Experiment.

We used a hierarchical blind docking protocol comprising PatchDock web server (ref Schneidman-Duchovny) for the first step with default parameters. The top 1000 solutions from PatchDock were refined and reranked using Firedock server (ref Schneidman-duchovny 2). The top 10 reranked solutions were optimized with RosettaDock as implemented in ROSIE (ref Lyskov) with the no-refine parameter. Consensus binding mode, illustrated in FIG. 2 was extracted from the top solutions.

NRP-1 and OBR Complex Detection in MBA-MB231 Breast Cancer Cell Line by Immunocytochemistry Using a PLA Technology The detection of NRP-1/OBR complex in human MDA-MB231 breast cancer cell line was assessed by proximity ligation assay (PLA) or duolink technology (www.olink.com). The detection of the NRP-1/OBR complex was assessed on MDA-MB231 cell line cultivated in normal human serum (human male AB plasma, USA origin, MDL number MFCD00165829 H4522 Sigma) and treated or not with Avastin 40 µg/ml final concentration for 48 h. The goal by using human serum was to mimic a physiologic condition during therapy with Avastin. The immunostained samples were analysed by the acquisition of the Z stacks through confocal microscopy on Zeiss LSM 700, Inverted confocal microscope. The acquired images were analyzed using Image J software for the quantification of NRP-1/OBR complex expressed by cells.

Results

By using a BioLayer Interferometry technology (BLI, http://www.fortebio.com), we were able to demonstrate a direct interaction between recombinant proteins leptin and NRP-1 (FIG. 1A). VEGF165 has been used as positive control of the experiment. Surprisingly, in contrast to other NRP-1 ligands, VEGF, and Sema3A known as competitors, leptin binds directly to NRP-1 but do not compete with VEGF binding and similarly VEGF does not prevent leptin binding to NRP-1. These observations suggest that leptin and VEGF should have a distinct binding domain.

Since BLI technology have shown that leptin and VEGF could interact with NRP-1 in non-competitive way and since we could demonstrate that leptin and VEGF form a complex in obese people tissue and by BLI technology using recombinant protein we assessed a docking of NRP-1 and leptin complexed with VEGF165. From the best consensus mode, peptide sequences SEQ ID NO:3 for leptin and SEQ ID NO:4 for NRP-1 have been identified (FIG. 2). The Leptin (OB) binding domain (SEQ ID:3) to NRP-1 (SEQ ID:2) was validated by BLI using a synthetized peptide (SEQ ID:3) and the extracellular domain of the recombinant protein NRP-1 from RnD systems (FIG. 3).

Since we have demonstrated that VEGF play a negative feed-back regulatory role for leptin signaling and since we demonstrated that Avastin increased MDA-MB231 cell migration, this raises the question of whether of not the Avastin effect occurs or not through the increase of NRP-1/OBR complex formation? Interestingly, compared to MDA-MB231 cell line cultivated in human serum, cells cultivated in the same condition and treated with Avastin40 mg/ml presented a high number of NRP-1/OBR complex which my explain the increase of the migration of the cells.

REFERENCES

Throughout this application, various references describe the state of the art to which this invention pertains. The disclosures of these references are hereby incorporated by reference into the present disclosure.

Münzberg H, Morrison C D. Structure, production and signaling of leptin. Metabolism. 2015 January; 64(1):13-23.

Belaid Z, Hubint F, Humblet C, Boniver J, Nusgens B, Defresne M P. Differential expression of vascular endothelial growth factor and its receptors in hematopoietic and fatty bone marrow: evidence that neuropilin-1 is produced by fat cells. Haematologica. 2005 March; 90(3): 400-1.

Fujisawa H. Discovery of semaphorin receptors, neuropilin and plexin, and their functions in neural development. J Neurobiol. 2004 April; 59(1):24-33.

Soker S, Takashima S, Miao H Q, Neufeld G, Klagsbrun M. Neuropilin-1 is expressed by endothelial and tumor cells as an isoform-specific receptor for vascular endothelial growth factor. Cell. 1998 Mar. 20; 92(6):735-45.

Tordjman R, Lepelletier Y, Lemarchandel V, Cambot M, Gaulard P, Hermine O, Romeo P H. A neuronal receptor, neuropilin-1, is essential for the initiation of the primary immune response. Nat Immunol. 2002 May; 3(5):477-82

Ghez D, Lepelletier Y, Lambert S, Fourneau J M, Blot V, Janvier S, Arnulf B, van Endert P M, Heveker N, Pique C, Hermine O. Neuropilin-1 is involved in human T-cell lymphotropic virus type 1 entry. J Virol. 2006 July; 80(14):6844-54.

Belaid-Choucair Z, Lepelletier Y, Poncin G, Thiry A, Humblet C, Maachi M, Beaulieu A, Schneider E, Briquet A, Mineur P, Lambert C, Mendes-Da-Cruz D, Ahui M L, Asnafi V, Dy M, Boniver J, Nusgens B V, Hermine O, Defresne M P. Human bone marrow adipocytes block granulopoiesis through neuropilin-1-induced granulocyte colony-stimulating factor inhibition. Stem Cells. 2008 June; 26(6):1556-64

He Z, Tessier-Lavigne M. Neuropilin is a receptor for the axonal chemorepellent Semaphorin III. Cell. 1997 Aug. 22; 90(4):739-51.

Perera, C. N., Chin, H. G., Duru, N., and Camarillo, I. G. (2008a). Leptin-regulated gene expression in MCF-7 breast cancer cells: mechanistic insights into leptin-regulated mammary tumor growth and progression. J. Endocrinol. 199, 221-233.

Perera, C. N., Spalding, H. S., Mohammed, S. I., and Camarillo, I. G. (2008b). Identification of proteins secreted from leptin stimulated MCF-7 breast cancer cells: a dual proteomic approach. Exp. Biol. Med. Maywood N.J. 233, 708-720.

Yihai Cao. Angiogenesis and Vascular Functions in Modulation of Obesity, Adipose Metabolism, and Insulin Sensitivity. Cell Metab. 2013 Oct. 1; 18(4):478-89.

Ruben Rene Gonzalez-Perez, Viola Lanier and Gale Newman. Leptin's Pro-Angiogenic Signature in Breast Cancer. *Cancers* 2013, 5, 1140-1162.

Xu L, Duda D G, di Tomaso E, Ancukiewicz M, Chung D C, Lauwers G Y, Samuel R, Shellito P, Czito B G, Lin P C, Poleski M, Bentley R, Clark J W, Willett C G, Jain R K. Direct evidence that bevacizumab, an anti-VEGF antibody, up-regulates SDF 1 alpha, CXCR4, CXCL6, and neuropilin 1 in tumors from patients with rectal cancer. Cancer Res. 2009 Oct. 15; 69(20):7905-10.

Patchdock: Duhovny D, Nussinov R, Wolfson H J. Efficient Unbound Docking of Rigid Molecules. In Gusfield et al., Ed. Proceedings of the 2'nd Workshop on Algorithms in Bioinformatics (WABI) Rome, Italy, Lecture Notes in Computer Science 2452, pp. 185-200, Springer Verlag, 2002

Patchdock Server: Schneidman-Duhovny D, Inbar Y, Nussinov R, Wolfson H J. PatchDock and SymmDock: servers for rigid and symmetric docking. Nucl. Acids. Res. 33: W363-367, 2005.

Firedock: N. Andrusier, R. Nussinov and H. J. Wolfson. FireDock: Fast Interaction Refinement in Molecular Docking. Proteins (2007), 69(1):139-159.

Firedock server: E. Mashiach, D. Schneidman-Duhovny, N. Andrusier, R. Nussinov, H. J. Wolfson. FireDock: a web server for fast interaction refinement in molecular docking. Nucleic Acids Res. (2008), 36 (Web Server issue): W229-32.

Rosetta dock server: Lyskov S., Gray J. J. "The RosettaDock server for local protein-protein docking" Nucleic Acids Research 36 (Web Server Issue), W233-W238 (2008).

The invention claimed is:

1. An isolated, a synthetic or a recombinant polypeptide capable of inhibiting the binding between leptin and NRP-1, wherein the polypeptide consists of the amino acid sequence of SEQ ID NO:3 (ENLRDLLHVLAFSKSCHLPWAS-GLETL) or SEQ ID NO:4 (EGNKPVLFQGNTNPTDVY-VAVFPK), and wherein the polypeptide is fused to at least one heterologous polypeptide.

2. A nucleic acid encoding the polypeptide fused to the at least one heterologous polypeptide of claim 1.

3. The nucleic acid of claim 2 which is included in a suitable vector.

4. An isolated host cell comprising the nucleic acid of claim 2.

5. A pharmaceutical composition comprising the polypeptide fused to the at least one heterologous polypeptide of claim 1 or a nucleic acid encoding the polypeptide fused to the at least one heterologous polypeptide.

6. The nucleic acid of claim 3 wherein the vector is a plasmid, a cosmid, an episome, an artificial chromosome, a phage or a viral vector.

* * * * *